(12) United States Patent
Eskin et al.

(10) Patent No.: US 7,581,436 B2
(45) Date of Patent: Sep. 1, 2009

(54) METHOD FOR OPERATING A COUETTE DEVICE TO CREATE AND STUDY EMULSIONS

(75) Inventors: Dmitry Eskin, Edmonton (CA); Shawn David Taylor, Edmonton (CA); Hussein Alboudwarej, Walnut Creek, CA (US); Joao Felix, Houston, TX (US); Geza Horvath Szabo, Edmonton (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 12/020,388

(22) Filed: Jan. 25, 2008

(65) Prior Publication Data

US 2009/0188304 A1 Jul. 30, 2009

(51) Int. Cl.
*G01N 11/14* (2006.01)
(52) U.S. Cl. .................................. 73/54.31
(58) Field of Classification Search ............ 73/54.28, 73/54.31–54.35; 366/269
See application file for complete search history.

(56) References Cited

U.S. PATENT DOCUMENTS

| | | | | |
|---|---|---|---|---|
| 2,295,740 A * | 9/1942 | Keen | ............................. | 261/93 |
| 3,456,494 A * | 7/1969 | Zimmer | ....................... | 73/54.33 |
| 4,077,251 A | 3/1978 | Winter | | |
| 4,174,907 A * | 11/1979 | Suh et al. | ..................... | 366/279 |
| 5,209,108 A * | 5/1993 | Shackelford | ............... | 73/54.28 |
| 5,306,734 A | 4/1994 | Bass et al. | | |
| 5,370,824 A * | 12/1994 | Nagano et al. | ................. | 516/69 |
| 5,394,738 A | 3/1995 | Bass et al. | | |
| 5,445,179 A | 8/1995 | Di Lullo et al. | | |
| 5,538,191 A * | 7/1996 | Holl | ............................... | 241/1 |
| 5,959,194 A | 9/1999 | Nenniger | | |
| 5,998,493 A | 12/1999 | Mitchell et al. | | |
| 6,471,392 B1 * | 10/2002 | Holl et al. | ..................... | 366/279 |
| 6,742,774 B2 * | 6/2004 | Holl | ............................ | 261/83 |
| 6,745,961 B2 | 6/2004 | Korstvedt | | |
| 6,752,529 B2 * | 6/2004 | Holl | ............................ | 366/279 |
| 6,807,849 B1 | 10/2004 | Reed et al. | | |
| 6,874,353 B2 | 4/2005 | Johnson et al. | | |
| 6,959,588 B2 | 11/2005 | Zougari et al. | | |

(Continued)

FOREIGN PATENT DOCUMENTS

JP 58002215 A1 1/1983

OTHER PUBLICATIONS

Phan-Thien, N. and Pham, D.C.: "Differential multiphase models for polydispersed suspensions and particulate solids", J. Non-Newtonian Fluid Mech., 72 (1997) 305-318.

(Continued)

*Primary Examiner*—John Fitzgerald
(74) *Attorney, Agent, or Firm*—Jay P. Sbrollini; Wayne I. Kanak

(57) ABSTRACT

A method for generating and characterizing an emulsion. The method provides a Couette device having first and second cylindrical members that define an annulus between them. The second cylindrical member is rotatably driven with respect to the first cylindrical member. Two or more substances each in a non-emulsified state are injected into the annulus. The Couette device is operated in a first mode to generate an emulsion from the two or more substances. The Couette device is also operated in a second mode to measure various attributes of the emulsion.

22 Claims, 1 Drawing Sheet

U.S. PATENT DOCUMENTS

| | | | |
|---|---|---|---|
| 6,994,330 B2* | 2/2006 | Holl | 261/92 |
| 7,150,183 B2 | 12/2006 | Kharrat et al. | |
| 2007/0022802 A1 | 2/2007 | Rogers et al. | |

OTHER PUBLICATIONS

Akroyd, Timothy James: "Continuous Flow Rheometry for Settling Slurries", Thesis, Chem. Eng., University of Adelaide, Nov. 2004.

Kleinstreuer, Clement.: "Engineering Fluid Dynamics—An Interdisciplinary Systems Approach", Cambridge University Press (1997) 234.

Hughmark, G.A.: "An Analysis of Turbulent Pipe Flow with Viscosity Variation in the Wall Region", A.I.Ch.E. Journal, vol. 21, No. 1, Jan. 1975, 187-189.

Krantz, W.B. and Wasan, D.T.: "A Correlation for Velocity and Eddy Diffusivity for the Flow of Power-Law Fluids Close to a Pipe Wall", Ind. Eng. Chem. Fundam. vol. 10, No. 30, 1971, 424-427.

Lewis, Gregory S. And Swinney, Harry L.: "Velocity structure functions, scaling, and transitions in high-Reynolds-number Couette-Taylor flow", Physical Review E, vol. 59, No. 5, May 1999, 5457-5467.

Schlichting, Herrmann and Gersten, Klaus: "Boundary-Layer Theory", Springer, 8th Rev., 2000, 556-567.

Kreiger, Irvin M. and Elrod, Harold: "Direct Determination of the Flow Curves of Non-Newtonian Fluids. II. Shearing Rate in the Concentric Cylinder Viscometer", Journal of Applied Physics, vol. 24, No. 2, Feb. 1953, 134-136.

Lathrop, Daniel P., Fineberg, Jay, and Swinney, Harry L.: "Transition to shear-driven turbulance in Couette-Taylor flow", Physical Review A, vol. 46, No. 10, Nov. 15, 1992, 6390-6408.

Dodge, D.W. And Metzner, A.B.: "Turbulent Flow of Non-Newtonian Systems", A.I.Ch.E. Journal, vol. 5, No. 2, Jun. 1959, 189-204.

Krieger, Irvin M. And Maron, Samuel H.: "Direct Determination of the Flow Curves of Non-Newtonian Fluids", Journal of Applied Physics, vol. 23, No. 1, Jan. 1952, 147-149.

* cited by examiner

METHOD FOR OPERATING A COUETTE DEVICE TO CREATE AND STUDY EMULSIONS

BACKGROUND OF THE INVENTION

1. Field of the Invention

This invention relates broadly to Couette devices. More particularly, this invention relates to methods for using Couette devices to study emulsion fluid flow.

2. Description of the Related Art

A fluid is a substance that continually deforms or flows under an applied shear stress. It may contain liquids, gases, and solids, and generally takes on the shape of the container in which it is housed. When a fluid is transported through a pipe or tube, a number of properties of the fluid (such as temperature, pressure, and viscosity) may change depending on both the external constraints and the composition of the fluid. An emulsion is a fluid that consists of a mixture of at least two fluid phases that do not or only partially blend with each other. In a two-phase emulsion, one fluid (the dispersed phase) is dispersed within the other (the continuous phase). The creation of an emulsion from separate phases requires stirring, shaking, or some other form of energy input (microemulsions are not considered in this context). The process by which emulsions are created is called emulsification.

In an emulsion, the degree and uniformity of dispersion of the dispersed phase within the continuous phase will generally depend on the nature of the fluid phases of the emulsion, the rate of mixing, and the length of time that the fluid phases are mixed. If the interfacial tension between the dispersed and continuous phases of an emulsion is low or the kinetic stability of the thin liquid films between the approaching emulsion droplets is low, then the emulsion could be unstable. Over time, the components of an unstable emulsion tend to separate if the mixing, stirring, or shaking is ceased.

An emulsion's viscosity measurement represents its resistance to flow. This characteristic is frequently tested because it can directly affect the operation and performance of an industrial device. However, an emulsion's viscosity varies according to the specific proportions of its components and the extent to which they are mixed. Therefore, an emulsion's viscosity may vary under different flow conditions because the degree of emulsification (mixing) may vary in accordance with the flow conditions.

An emulsion's viscosity is measured with a rheometer or viscometer. One such device frequently used in the art is a Couette device. A cylindrical Couette device has an outer hollow cylinder and an inner cylinder that together define an annulus in the space between the exterior surface of the inner cylinder and the interior surface of the outer cylinder. The annulus is filled with an emulsion and the cylinders rotate relative to one another. This rotation imposes shear stresses on the emulsion resulting in flow. The properties of the fluid flow vary depending on the parameters imposed on the emulsion by the device (such as temperature, pressure, and rate of shear (angular velocity)), as well as the characteristics of the fluid itself (such as its viscosity and density). Examples of Couette devices are shown in U.S. Pat. No. 6,959,588 B2 and U.S. Pat. No. 5,959,194.

Both wide and narrow gap rheometers may be used to determine an emulsion's viscosity. The gap size in a cylindrical Couette device refers to the distance between the outer surface of the inner cylinder and the inner surface of the outer cylinder. A smaller (narrow) gap usually promotes laminar flow in the device by inducing high shear rates throughout the fluid. A wide gap provides lower shear stresses, and can operate in a turbulent fluid flow regime that more closely resembles emulsification conditions in industrial equipment, such as in a pipeline or centrifugal pump.

Industrial devices frequently transport emulsions containing mixtures of oil, water, or other substances. The performance of an industrial device is often linked to a number of properties of the emulsion, such as its viscosity. Emulsions are thus frequently created and tested to evaluate their properties when subjected to the kinds of shear stresses, temperatures, pressures, and other flow parameters imposed by industrial devices in the field. It is often difficult to measure an emulsion's viscosity immediately after a sample is taken from a field device. Under laboratory conditions, emulsions are frequently generated in one device and then tested in another device, and care must be taken so that the emulsion's properties will not change significantly as it is transferred from the generating device to the testing device.

BRIEF SUMMARY OF THE INVENTION

The present invention is directed to a method for generating and characterizing an emulsion in a Couette device. The Couette device has first and second cylindrical members defining an annulus between them. The first cylindrical member is stationary while the second cylindrical member is rotatably driven with respect to the first cylindrical member. Sensors, which are preferably mounted to the drive shaft of the rotating cylindrical member, measure the torque placed on the rotating cylindrical member as well as the angular velocity of the rotating cylindrical member as it rotates. At least two fluids, each in a non-emulsified state, are injected into the annulus of the Couette device. The Couette device is operated in a first mode to mix the fluids into an emulsified state. In the first mode, as the cylindrical members of the Couette device rotate relative to one another, a shear stress is imposed on the two fluids, causing them to mix and flow. One of the two fluids becomes the continuous phase and the other the dispersed phase. The dispersed phase is "dispersed" within the continuous phase. After the emulsion is created by operation of the Couette device, the Couette device is operated in a second mode to characterize the emulsion, which preferably determines either the viscosity if the emulsion is Newtonian or the rheology parameters if the emulsion is non-Newtonian.

In the preferred embodiment, several operating parameters of the Couette device in the first mode of operation are derived based upon known field conditions, energy dissipation rate equations, and turbulent flow models. In particular, it is assumed that the energy dissipation rate of the Couette device in the first mode of operation will match or approximately equal the energy dissipation rate of the field device. These factors allow the derivation of an initial set of conditions, including an initial angular velocity. This initial angular velocity is used to create the emulsion. In a second embodiment, the angular velocity is varied during the first mode of operation to account for variations in the energy dissipation rate as the emulsion is being formed. It is intended that the first mode of operation generate an emulsion having flow properties similar to that encountered in the field.

In the preferred embodiment, the second mode operations of the Couette device characterize the emulsion generated in the first mode by varying the angular rotation speed of the inner cylinder in a given range and measuring the corresponding torque at a number of angular rotation speeds. The torque and angular rotation speed data are then used in conjunction with known correlations and turbulent flow models to derive the emulsion's viscosity or rheology parameters. The measured flow characteristics of the emulsion in the Couette device can then be used to predict a system's performance in moving or transporting the emulsion (e.g., the expected pressure gradient in an industrial pipe at various diameters).

DETAILED DESCRIPTION OF THE INVENTION

Figure 1:
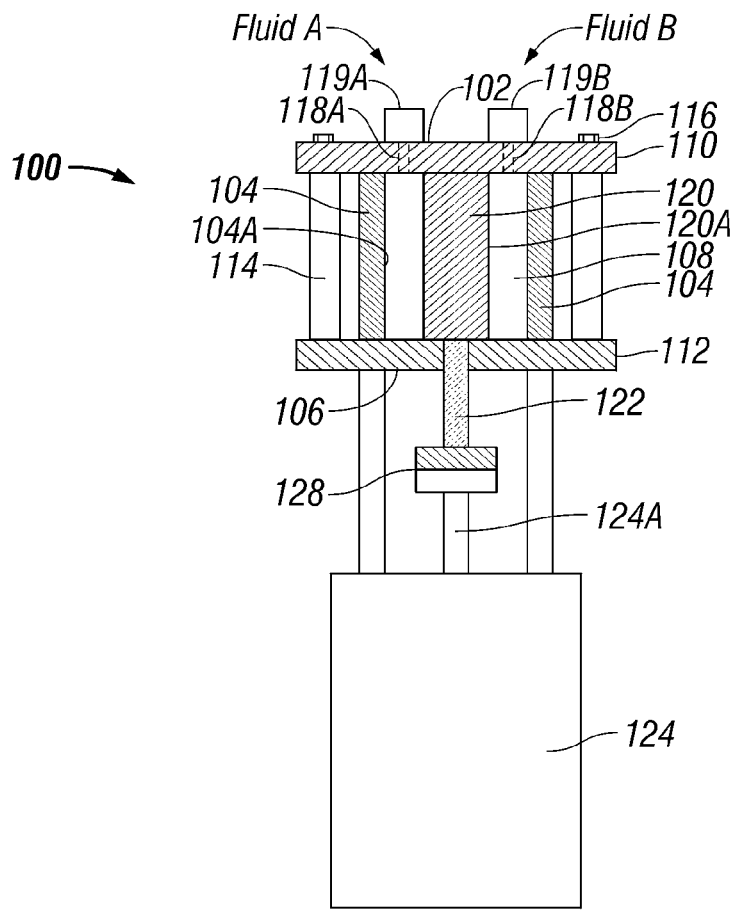
FIG. 1 is a side cross section view of a cylindrical Couette device for use in the method of the present invention.

FIG. 1 illustrates an exemplary cylindrical Couette device 100, which includes a top wall 102, outer cylinder 104, inner cylinder 120, and bottom wall 106 that define the boundary of an annulus 108 disposed between the inner surface 104A of the outer cylinder 104 and the outer surface 120A of the inner cylinder 120. The Couette device 100 has top and bottom retaining plates 110, 112 set apart by spacers 114 and mechanically secured, for example, by nuts and bolts 116. At least two fluids, each in an unemulsified state (labeled as Fluid A and Fluid B in FIG. 1), are injected into the annulus 108 preferably through one or more fluid paths (e.g., two shown as 118A, 118B). For example, Fluid A can be a crude oil and Fluid B can be water. In the preferred embodiment, the fluid paths 118A, 118B are channels running through the top retaining plate 110 into the annulus 108. The fluid paths 118A, 118B are preferably connected to valves 119A, 119B that provide for flow control of the two fluids into the annulus 108 (and possibly for flow control of the emulsion therefrom).

The inner cylinder 120 is mounted on bearings and is coaxial with the outer cylinder 104. The outer cylinder 104 is fixed in position and thus remains stationary. The inner cylinder 120 rotates independently of the outer cylinder 104. A shaft 122 extends down from the bottom of the inner cylinder 120. A motor 124 has an output shaft 124A that is mechanically coupled to the shaft 122 by means of a coupling device 128, which can be a magnetic coupler, a rigid coupler, a flexible coupler, or other suitable coupling mechanism. In the preferred embodiment, the motor 124 can operate at variable speeds for rotating the inner cylinder 120 at different angular velocities.

Instrumentation can be added to the Couette device 100 as needed. For example, devices for heating and/or cooling the fluids within the annulus 108 of the Couette device 100 may be added. Such devices may be used in conjunction with the injecting of the fluids into the annulus 108 to achieve a predetermined pressure in the annulus 108. Pumps (not shown) are used to transfer the fluids into the annulus 108. The pumps define and maintain the pressure of the system. The annulus 108 can be filled with the fluids to be emulsified either prior to or during rotation of the inner cylinder 120. In the event that the annulus 108 is filled prior to the start of rotation, a number of top valves (not shown) are closed to seal off, isolate, and maintain the pressure inside of the annulus 108, and no fluids are allowed into or out of it.

Alternatively, one of the fluids to be emulsified may be injected into the annulus 108 before the inner cylinder 120 is rotated, and the other one of the fluids to be emulsified may be injected into the annulus 108 during the rotation of the inner cylinder 120. Adding the other fluid during the rotation of the inner cylinder 120 is preferable because it allows a user to control which of the fluids becomes the continuous phase and which becomes the dispersed phase (e.g. a given ratio of oil and water can become an oil-in-water mixture or a water-in-oil mixture depending on which of the fluids is gradually added to the other). A wide range of volume fractions can produce both oil-in-water (O/W) and water-in-oil (W/O) emulsions depending on the emulsification procedure. As it may be difficult to assess the exact conditions in industrial settings, producing the same type of emulsion as that observed in industrial practice often requires forming both types of emulsions (e.g. O/W by injecting oil into water and W/O by injecting water into oil). These tests will yield two estimates for the emulsion viscosity. Typically, the viscosity for an O/W emulsion is different from the viscosity of a W/O emulsion of the same volume fraction. The higher viscosity value may then be used to estimate the maximum possible pressure gradient expected in a field device.

At least one temperature sensor 126 (FIG. 2) and at least one pressure sensor 127 can be mounted adjacent the annulus 108 to measure fluid temperature and pressure therein. In the preferred embodiment, the rotational speed of the inner cylinder 120 is measured through the use of a proximity sensor 130, which measures the rotational speed of the shaft 122 mechanically coupled to the inner cylinder 120. A torque sensor 132 is coupled to the shaft 122 to measure the torque applied to the shaft 122, which is indicative of the shear stress in the fluid. The shear rate can be varied by changing the relative rotational speed of the inner cylinder 120 with respect to the outer cylinder 104.

To generate the emulsion, the Couette device 100 is operated in a first mode to stir the fluids disposed within the annulus 108 into an emulsified state. In the first mode, as the inner cylindrical member 120 rotates relative to the stationary outer cylinder 104, a shear stress is imposed on the two fluids, causing a dispersion of one fluid into another, as well as fluid flow. One of the two fluids becomes the continuous phase and the other the dispersed phase. The dispersed phase is "dispersed" throughout the continuous phase. After the emulsion is created by operation of the Couette device 100, the Couette device 100 is operated in a second mode to characterize the emulsion by determining its viscosity or rheology.

In the preferred embodiment, the Couette device 100 is operated in the first mode to create the emulsion based on parameters derived from known field conditions, energy dissipation rate equations, and turbulent flow models. One generally known field condition is the percentage or concentration of the fluids comprising the emulsion. The annulus 108 of the Couette device 100 is injected with the fluids in these concentrations. Typically, the concentrations of the fluids are measured by volume to ensure that they are injected into the annulus 108 in the proper ratio, but their molar or mass ratios may also be used. Several other known characteristics from which the first mode operational parameters of the Couette device 100 are derived include the fluids' viscosities, pressures, and temperature ranges in the field. In addition, the flow velocity of an emulsion in/through a particular field device (such as the cross section of a pipe) is also known. The time to form an emulsion is usually short, and varies between seconds and minutes depending on the shear rates imposed on the fluids. Raw materials encountered in the field flowing under high shear rates tend to form emulsions relatively quickly when they are transported through pumps and/or pipelines.

These known quantities and factors are used to derive the first mode operating parameters of the Couette device 100. One of the first mode operating parameters is the initial angular velocity, $\Omega_{create}$, at which to rotate the inner cylinder 120 for generating the emulsion. The goal is to generate an emulsion similar to one encountered in the field. Creating a representative emulsion is a function of not only simulating the respective concentrations, temperatures, and pressures of the fluids, but also the rate at which they are mixed, which affects the interfacial boundary layers between the fluids, the fluid particle size, and the stability of the emulsion. The derivation of the initial angular velocity, $\Omega_{create}$, is discussed below.

It is assumed that the energy dissipation rate, $\epsilon$, of the first mode operations of the Couette device 100 will match or approximately equal the energy dissipation rate of the field device since a representative emulsion will be flowing under similar conditions. Subjecting fluids to a pressure, temperature, surface type, and shear comparable to field conditions to produce a representative emulsion enables a more realistic simulation of the flow conditions in the field, and can more accurately predict the performance of an industrial device or system through which the emulsion is transported.

In the preferred embodiment, the initial operating parameters for the Couette device 100 are determined with the intent of simulating an emulsion's flow in a pipe. An estimation of the initial angular velocity, $\Omega_{create}$, and the corresponding torque, $T_{create}$, may be derived from a momentum equation, friction factor correlation, and pipe flow equation. In a pipe, the energy dissipation rate may be represented as a function of the pressure gradient in the pipe multiplied by the superficial flow velocity of the emulsion through the pipe. The superficial flow velocity encountered in the field is a known quantity. The pressure gradient in the pipe, $$\frac{dp}{dx},$$

may be estimated by a momentum equation based on an empirical friction factor (f) as follows:

$$\frac{dp}{dx} = -\rho_e f \frac{U^2}{2D} \quad (1)$$

where D is the pipe's inner diameter, f is the friction factor, U is the superficial flow velocity of the emulsion in the pipe, $\rho_e = \rho_d \phi + \rho_c (1-\phi)$ is the emulsion density, $\rho_c$ is the density of a continuous phase, $\rho_d$ is the density of a dispersed phase, and $\phi$ is the volume concentration of the dispersed phase. The friction factor, f, is calculated by the Colebrook-White correlation based on the Moody diagram (Blevins, 1992) (Blevins R. D., *Applied Fluid Dynamics Handbook*; Krieger Publishing Company: Malabar, 1992):

$$\sqrt{\frac{1}{f}} = -2\log\left(\frac{2.51}{Re\sqrt{f}} + \frac{k_s}{2.7D}\right) \quad (2)$$

where Re is the pipe Reynolds number and $k_s$ is the pipe surface micro-roughness. The energy dissipation rate, $\epsilon$, in a pipe may be estimated according the equation:

$$\varepsilon = \frac{dp}{dx} U \quad (3)$$

In a cylindrical Couette device, the energy dissipation rate may be expressed as a function of the angular velocity of at least one of the cylindrical members, the corresponding torque placed on the cylindrical member by the emulsion as it experiences a shear stress due to its viscosity (resistance to flow), the inner and outer diameters of the cylindrical members, and the rotor length of the Couette device. Setting the two expressions for energy dissipation rate equal gives the following equation:

$$\varepsilon = \frac{dp}{dx} U = \frac{\Omega_{create} T_{create}}{\pi (b^2 - a^2) L} \quad (4)$$

where $T_{create}$ is an estimate of the torque that will initially be applied to the inner cylinder, a and b are, respectively, the internal and external radii of the Couette device, and L is the rotor length of the Couette device. All values are known except for $\Omega_{create}$ and $T_{create}$. Initial values for $\Omega_{create}$, $T_{create}$ are determined by a numerical model of a turbulent flow in a Couette device at an estimated emulsion viscosity, $\eta_e$, such that they satisfy Equation (4).

The estimated emulsion viscosity, $\eta_e$, is calculated based upon the known viscosities of the fluids to be mixed according to known correlations, an example of which is shown by Phan-Thien and Pham, "Differential multiphase models for polydispersed suspensions and particulate solids", Journal of Non-Newtonian Fluid Mechanics 72, 305-318, (1997):

$$\eta_r^{\frac{2}{5}} \left[\frac{2\eta_r + 5K}{2 + 5K}\right]^{\frac{3}{5}} = \frac{1}{1 - \phi} \quad (5)$$

where $K = \eta_d/\eta_c$, $\eta_d$ is the viscosity of the fluid that will become the dispersed phase, $\eta_c$ is the viscosity of the fluid that will become the continuous phase, $\eta_r = \eta_e/\eta_c$, $\eta_e$ is the viscosity of the emulsion, and $\phi$ is the volume concentration of the dispersed phase. This initial viscosity estimation may differ significantly from the measured viscosity of the emulsion (further discussed below). If so, then one or more iterative measurements may be performed, and the viscosity measured for each iteration may be used for the subsequent iteration. One embodiment describing this process is further discussed below in paragraph 0037.

For each $\Omega_{create}$, a corresponding $T_{create}$ is calculated. The angular velocity, $\Omega_{create}$, is varied numerically until the pair $\Omega_{create}$, $T_{create}$ satisfies Equation (4) and corresponds to the given energy dissipation rate.

Alternatively, the energy dissipation rate can correspond to a more complicated field device. In such cases, modern computational fluid dynamics (CFD) codes such as Fluent or CFX (available from ANSIS International LLC of New York, N.Y., USA) provide a mechanism to compute and model complex flow patterns in an industrial device such as a centrifugal pump, and to estimate the energy dissipation rate therein (see, for example, Huang S., Islam M. F., Liu P. F., *International Journal of Computational Fluid Dynamics* 20 (5), 309-314, 2006, herein incorporated by reference in its entirety). An average value of the energy dissipation rate calculated by a CFD code can be substituted into Equation (4) to solve for $\Omega_{create}$, $T_{create}$ for emulsion generation and characterization in the Couette device as described above. Established CFD models in the art for other devices can be used to provide the necessary energy dissipation rate calculation required for the estimation of $\Omega_{create}$ and $T_{create}$ in the first mode.

The Couette device 100 is preferably operated in the first mode until the torque measured by the torque sensor 132 becomes constant, which indicates that the fluids have become fully emulsified. Torque measurements are taken by the torque sensor 132 and input to the control unit 138 while the inner cylinder 120 is rotated. As the fluids emulsify, the changes in the emulsion's viscosity are reflected in the torque measurements sensed by the torque sensor 132. When the torque measurements level off and remain constant at a given angular velocity $\Omega_{create}$, the Couette device 100 is operated in a second mode.

After the emulsion is generated, the Couette device 100 is operated in a second mode to determine the emulsion's viscosity or rheological characteristics using torque and angular rotation speed data. The range of angular rotation speeds at which to operate the Couette device 100 when testing the emulsion are preferably set such that the minimum speed provides a turbulent flow regime, and the maximum speed selected equals twice the minimum speed. The minimum angular velocity, $\Omega_{min}$, providing a stable turbulent flow regime should produce a Reynolds Number (Re) greater than 13,000, and may be derived from the following equation:

$$Re = \frac{\rho_e \Omega_{min} a(b-a)}{\eta_e} \geq 13,000 \quad (6)$$

A representative flow equation for the emulsion is determined by running a turbulent flow model that assumes a power-law rheology. The shear stress is calculated from such a model according the following equations:

$$\tau = \kappa \dot{\gamma}^n + \tau_{turb} = \frac{T}{2\pi L r^2}; \quad (7)$$

$$\dot{\gamma} = \left(\frac{du}{dr} - \frac{u}{r}\right);$$

where $\tau$ is the shear stress at a radius r of the Couette device, $\tau_{turb}$ is the turbulent shear stress determined by a turbulence model (cited below), $\dot{\gamma}$ is the shear rate corresponding to the shear stress, u is a circumferential flow velocity, and $\kappa$, n are the variables that match the above equation (derived from the calculated dependence of the function $T(\Omega)$ to the torque values measured at various angular velocities within the angular velocity range. The first component, $\kappa \dot{\gamma}^n$, of the above equation for the shear stress determines only the laminar component of the shear stress, and in a turbulent flow, determines the total stress only within the laminar boundary layer.

The second component, $\tau_{turb}$, may be calculated from a number of different turbulence models (see, for example, R. Peyret, T. D. Taylor, *Computational Methods for Fluid Flow*, Springer-Verlag, New York Heydelberg, Berlin, 1983, herein incorporated by reference in its entirety). Another well known model is the "k–ϵ" model. This mixing length model is based on the assumption that the turbulent shear stress is a function of both the distance from a given point in a flow to the wall, and the local shear rate. According to the k–ϵ model, the turbulence shear stress, $\tau_{turb}$, is a function of the turbulence kinetic energy and the energy dissipation rate. The k–ϵ model requires solving two differential transport equations (an equation describing the distribution of the turbulent kinetic energy in a flow domain and an equation describing the distribution of the energy dissipation rate in the flow domain). (See, for example, R. Peyret, T. D. Taylor, *Computational Methods for Fluid Flow*, Springer-Verlag, New York Heydelberg, Berlin, 1983, incorporated herein by reference in its entirety).

The solution of Equation (7) is then reduced to determining the values of ($\kappa$, n) that match Equation (7) with the measured dependence of the torque versus the angular velocity. The measured torque and angular velocity values are used to solve Equation (7) to produce a model equation representing the emulsion's flow. Equation (7) is solved iteratively by varying the rheology variables (k, n) until the calculated dependence $T(\Omega)$ fits the measured function determined by the measured data ($\Omega$, T). In the preferred embodiment, the torque is measured in several (less than ten) defined measured points spanning the entire angular velocity range. If the emulsion turns out to be Newtonian (discussed below), then the variable 'n' will equal 1 or be close to 1 with a deviation of less than five percent.

Pressure Gradient Calculation Based on Flow Equation

For non-Newtonian emulsions, Equation (7):

$$\tau = \kappa \dot{\gamma}^n + \tau_{turb} = \frac{T}{2\pi L r^2};$$

$$\dot{\gamma} = \left(\frac{du}{dr} - \frac{u}{r}\right);$$

models the flow of an emulsion by expressing the shear stress as a function of the shear rate. Once values for (k, n) are obtained, Equation (7) may be used to predict the pressure gradient in a field device such as a pipe by using a known correlation based on one of the models for turbulent power law fluid flow in a pipe. See, for example, G. A. Hughmark, *An Analysis of Turbulent Pipe Flow with Viscosity Variation in the Wall Region*, AICHE Journal, Vol. 21 (1), pp. 187-189; W. B. Krantz, D. T. Wasan, *A Correlation for Velocity and Eddy Diffusivity for the Flow of Power-Law Fluids Close to a Pipe Wall*, Id. Eng. Chem. Fundam, Vol. 10 (3), 1971, pp. 424-427; D. W. Dodge, A. B. Metzner, *Turbulent Flow of Non-Newtonian Systems*, AICHE Journal, Vol. 5(2), 1959, pp. 189-204, each of which is incorporated herein by reference in its entirety.

The pipe pressure gradient for a power-law fluid flow can be calculated in the same manner as for a Newtonian flow per Equation (1). The friction factor in a smooth pipe is determined as a function of the Reynolds number and the power-law exponent 'n' as in (Dodge and Metzner, 1959):

$$\sqrt{\frac{1}{f}} = \frac{4}{n^{0.75}} \log[Re f^{1-\frac{n}{2}}] - \frac{0.4}{n^{1.2}} \quad (8)$$

where the Reynolds number is modified according to Dodge and Metzner (1959):

$$Re = \frac{8 \rho_e U^{2-n} D^n}{\kappa \left(6 + \frac{2}{n}\right)^n} \quad (9)$$

For Newtonian emulsions, Equation (7) is simplified because $\tau_{turb}$ equals zero and the variable 'n' equals one. After fitting Equation (7) to the ($\tau$, $\Omega$) data obtained, Equation (7) reduces to $\tau = \kappa \dot{\gamma}$ for a Newtonian emulsion. The viscosity (shear stress divided by shear rate) of the Newtonian emulsion will generally be constant and equal to '$\kappa$' regardless of the shear rate. The shear stress developed in a Newtonian emulsion will be linearly proportional to the applied shear rate. Therefore, a Newtonian emulsion's viscosity alone can be used to predict the pressure gradient in a field device such as a pipe by using the correlations of Equations (1)-(3) as set forth above.

Figure 2:
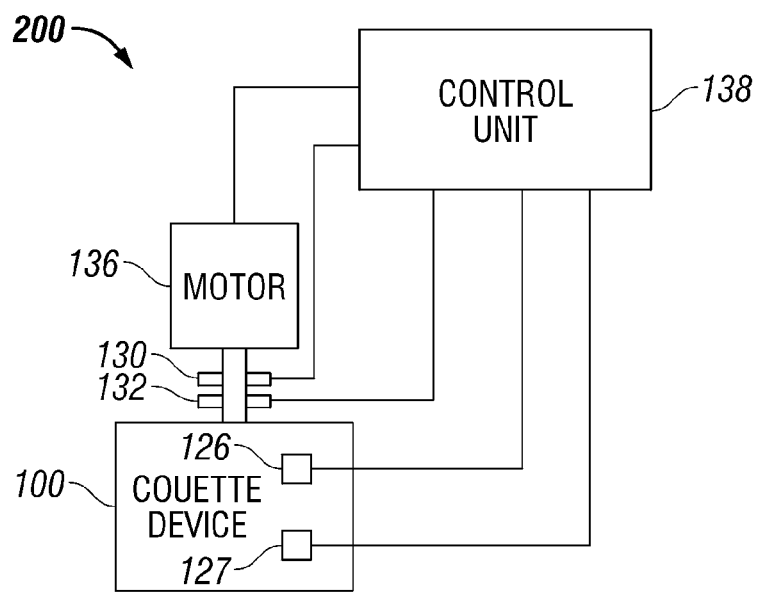
FIG. 2 is a schematic diagram of the Couette device of FIG. 1.

FIG. 2 is a schematic diagram of a Couette system 200. A control unit 138 is connected to the motor 136 of the Couette device 100. The temperature sensor 126, pressure sensor 127, proximity sensor 130 and torque sensor 132 are electronically coupled to the control unit 138. The control unit 138 can include a user interface that enables a user to operate the control unit 138 to drive the Couette device 100, measure the emulsion's characteristics, adjust the temperature and pressure of the emulsion, and increase/decrease the angular velocity of the inner cylinder 120. The control unit 138 may also be programmed to automatically carry out one or more of the operations of the Couette device 100 as described herein, including injection of the fluids into the annulus 108, heating and cooling of the fluid in the annulus 108, pressurization of the fluid in the annulus 108, inputting initial parameters, performing mathematical computations and derivations based on the input initial parameters and subsequent measured parameters, and operating the motor 136 to generate and/or characterize the emulsion according to the methods disclosed herein.

The above described procedure for calculating the initial angular velocity, $\Omega_{create}$, to create the emulsion assumes a constant energy dissipation rate. However, as the emulsion is generated, its viscosity increases as its components mix, which causes an increase in the energy dissipation rate. The increase in the energy dissipation rate during the emulsification process is a source of error in the above calculations, but may be taken into account by a more advanced measurement procedure in an alternative embodiment as discussed below. In an alternative embodiment, a more advanced measurement procedure is used to operate the Couette Device 100 in the first mode. Instead of rotating the inner cylinder 120 at a constant angular velocity, the angular velocity, $\Omega_{create}$, is varied to account for the varying energy dissipation rate as the emulsion is formed. The initial energy dissipation rate and angular velocity are calculated according to the method outlined above, but it is assumed that the initial mixture viscosity equals the viscosity of the continuous phase. The inner cylinder 120 is rotated at the angular velocity and the torque is monitored. As the emulsion is generated, the torque increases due to the increase in the mixture's viscosity, which changes the energy dissipation rate. The new energy dissipation rate is calculated via Equation (4):

$$\varepsilon = \frac{dp}{dx}U = \frac{\Omega_{create}T_{create}}{\pi(b^2 - a^2)L},$$

using the measured value for torque and the existing value for $\Omega_{create}$. A new value for $\Omega_{create}$ is generated via a numerical model for turbulent flow as cited above, (R. Peyret, T. D. Taylor, *Computational Methods for Fluid Flow*, Springer-Verlag, New York Heydelberg, Berlin, 1983) and the inner cylinder 120 is then rotated at the new angular velocity. Torque measurements are taken at the new angular velocity. If the torque continues to increase while rotating the inner cylinder 120 at the new angular velocity, then the computational process is repeated and the angular velocity is adjusted again.

In yet another embodiment, a number of additional operations may be performed to generate and characterize the emulsion with improved accuracy in many instances. For example, the pressure gradient, $$\frac{dp}{dx},$$

derived from the observed and calculated flow characteristics in the second mode as discussed above (as opposed to the estimated pressure gradient calculated from the momentum equation) can be used to recalculate the energy dissipation rate $$\left(\varepsilon = \frac{dp}{dx}U\right)$$

with a new emulsion viscosity estimation, and the above process is repeated. A new emulsion is generated by operating the Couette Device 100 in the first mode by first calculating a refined initial angular velocity from the new energy dissipation rate and then generating an emulsion using the refined initial angular velocity.

There have been described and illustrated herein several embodiments of a method for operating a Couette device to create and study emulsions. While particular embodiments of the invention have been described, it is not intended that the invention be limited thereto, as it is intended that the invention be as broad in scope as the art will allow, and that the specification be read likewise. Thus, while a cylindrical Couette device has been disclosed, it will be appreciated that other Couette devices could be used as well. While a cylindrical Couette device with a rotatably driven inner cylinder and a stationary outer cylinder has been disclosed, it will be appreciated that Couette devices in which both the inner and outer cylinders are rotatably driven may be used. In addition, while particular types of substances, namely, crude oil and water have been disclosed, it will be understood that virtually any fluid substances can be used. Also, while a method for predicting the pressure drop in a pipe based on an emulsion's characteristics in a Couette device has been disclosed, it will be recognized that the performance of numerous other field devices could be extrapolated from the data obtained from the emulsion generation and modeled Couette flow described herein. While particular turbulent flow correlations have been disclosed, it will be appreciated that any model of turbulent flow having a reasonable degree of accuracy could be employed for practical calculations. It will therefore be appreciated by those skilled in the art that yet other modifications could be made to the provided invention without deviating from and scope as claimed.

What is claimed is:

1. A method for generating and characterizing an emulsion, comprising:
    providing a device having first and second cylindrical members that define an annulus therebetween, wherein said second cylindrical member is rotatably driven with respect to said first cylindrical member;
    injecting at least two fluids, each in non-emulsified form, into said annulus;
    operating said device in a first mode whereby an emulsion is created, the emulsion including said at least two fluids, wherein at least one of the at least two fluids is in a continuous phase and at least one of the at least two fluids is in a dispersed phase; and subsequent to said first mode, operating said device in a second mode to measure at least one attribute of said emulsion.

2. The method of claim 1, wherein:
said device has at least one fluid path, said at least one fluid path being fluidly coupled to said annulus, and said injecting of said at least two fluids into said annulus is achieved through said at least one fluid path.

3. The method of claim 1, wherein:
said operating of said device in said first mode achieves a predetermined energy dissipation rate.

4. The method of claim 1, wherein said first cylindrical member is stationary.

5. The method of claim 1, wherein:
said device is operated in said first mode with said fluids at a predetermined temperature.

6. The method of claim 5, wherein:
said device is operated in said first mode with said fluids at a predetermined pressure.

7. The method of claim 1, wherein:
said operating of said device in said first mode includes rotating said second cylindrical member at a predetermined angular velocity $\Omega_{create}$.

8. The method of claim 7, wherein:
said predetermined angular velocity is chosen such that said device operates with an energy dissipation rate corresponding to an energy dissipation rate of a field device.

9. The method of claim 8, wherein:
said operating in said first mode includes measuring torque applied to said second cylindrical member at least until a constant torque is achieved at said predetermined angular velocity $\Omega_{create}$.

10. The method of claim 8, wherein:
said operating in said first mode includes rotating said second cylindrical member at said predetermined angular velocity $\Omega_{create}$, measuring torque at said predetermined angular velocity $\Omega_{create}$, and calculating a new energy dissipation rate from said measured torque and said predetermined angular velocity $\Omega_{create}$.

11. The method of claim 10, wherein:
said operating in said first mode further includes calculating a new angular velocity from a first model of turbulent flow based on said new energy dissipation rate and an estimated emulsion viscosity $\eta_e$, and rotating said second cylindrical member at said new angular velocity until a constant torque is achieved at said new angular velocity.

12. The method of claim 10, wherein:
said operating in said first mode further includes calculating a plurality of new energy dissipation rates and a plurality of corresponding new angular velocities at which to rotate said second cylindrical member, said device being operated in said first mode until a constant torque is measured at a given angular velocity.

13. The method of claim 8, wherein:
said predetermined angular velocity $\Omega_{create}$ is obtained from a first model of turbulent flow in said device at an estimated emulsion viscosity $\eta_e$, said first model of turbulent flow relating angular velocity and torque at said estimated emulsion viscosity $\eta_e$.

14. The method of claim 13, wherein:
said estimated emulsion viscosity $\eta_e$ is calculated according to the equation $$\eta_r^{\frac{2}{5}}\left[\frac{2\eta_r+5K}{2+5K}\right]^{\frac{3}{5}} = \frac{1}{1-\phi},$$

where $K=\eta_d/\eta_c$,
$\eta_r=\eta_e/\eta_c$
$\eta_d$ is the viscosity of said dispersed phase,
$\eta_c$ is the viscosity of said continuous phase,
$\eta_e$ is the estimated emulsion viscosity, and
$\phi$ is a volume concentration of said dispersed phase.

15. The method of claim 14, wherein:
said field device is a pipe, and said predetermined angular velocity $\Omega_{create}$ satisfies the equation $$\varepsilon = \frac{dp}{dx}U = \frac{\Omega_{create}T_{create}}{\pi(b^2-a^2)L},$$

where $$\frac{dp}{dx}$$

is the pressure gradient in a pipe at said estimated emulsion viscosity,
U is the superficial flow velocity of the emulsion in the pipe,
$T_{create}$ is the torque applied to said inner cylinder,
a and b are the internal and external radii of said device, and
L is the rotor length of said device.

16. The method of claim 13, further comprising:
deriving rheology parameters for said emulsion from a second model of turbulent flow.

17. The method of claim 16, further comprising:
using said rheology parameters to calculate a plurality of pressure gradients corresponding to a plurality of pipe diameters.

18. The method of claim 16, further comprising:
determining a pressure gradient in said pipe from said rheology parameters.

19. The method of claim 18, wherein:
said operating includes calculating an additional energy dissipation rate from said pressure gradient, using said additional energy dissipation rate to create a new emulsion, and testing said new emulsion for at least one rheological parameter.

20. The method of claim 16, wherein:
said rheology parameters are derived by
i) rotating said second cylindrical member at a plurality of angular velocities,
ii) measuring a plurality of torque values corresponding to said plurality of angular velocities,
iii) applying said plurality of angular velocities and corresponding measured torque values to said first model of turbulent flow.

21. The method of claim 20, wherein:
said second model of turbulent flow model is represented by equations $$\tau = \kappa\dot{\gamma}^n + \tau_{turb} = \frac{T}{2\pi Lr^2}, \text{ and}$$

-continued
$$\dot{\gamma} = \left(\frac{du}{dr} - \frac{u}{r}\right),$$

where $\tau$ is a shear stress on said emulsion at a radius r within said device, $\kappa$, n are variables that match said plurality of angular velocities and corresponding measured torque values to said second model of turbulent flow, T is the torque applied to the inner cylinder, L is the length of the inner cylinder, $\tau_{turb}$ is a turbulent shear stress, $\dot{\gamma}$ is a shear rate corresponding to said shear stress $\tau$, and u is a circumferential flow velocity.

22. The method of claim 20, wherein:

said plurality of angular velocities are within a predetermined range bounded by a minimum angular velocity and a maximum angular velocity, said minimum angular velocity producing a Reynolds number that exceeds 13,000, and said maximum angular velocity being equal to twice the value of said minimum angular velocity.

* * * * *